United States Patent [19]

Mullaly

[11] Patent Number: 4,509,797

[45] Date of Patent: Apr. 9, 1985

[54] WHEEL CHAIR RESTRAINT

[76] Inventor: Maxine M. Mullaly, 64 Larch Rd., Sayre, Pa. 18840

[21] Appl. No.: 514,483

[22] Filed: Jul. 18, 1983

[51] Int. Cl.³ ............................................. A47C 31/00
[52] U.S. Cl. .................................... 297/466; 297/467
[58] Field of Search ................ 49/466, 465, 464, 427, 49/467

[56] References Cited

U.S. PATENT DOCUMENTS

| | | | |
|---|---|---|---|
| 3,136,581 | 6/1964 | Caballero | 297/465 |
| 3,181,530 | 5/1965 | Storey | 297/465 X |
| 4,145,082 | 3/1979 | Daley et al. | 297/466 |
| 4,170,991 | 10/1979 | Kelia | 297/467 X |
| 4,190,287 | 2/1980 | Lemisch et al. | 297/466 |
| 4,192,546 | 3/1980 | Smith | 297/466 |

FOREIGN PATENT DOCUMENTS

| | | | |
|---|---|---|---|
| 1238617 | 4/1967 | Fed. Rep. of Germany | 297/466 |
| 1590172 | 5/1981 | United Kingdom . | |

Primary Examiner—Philip C. Kannan
Attorney, Agent, or Firm—Donald A. Kettlestrings

[57] ABSTRACT

A flexible restraint made of cloth or fabric material for use with wheel chairs and other chairs having seats and backs and wherein the restraint is attached to the chair. Restraining strap portions of the restraint are wrapped upwardly about inner portions of the patient's thighs and at least partially over the thighs to be secured to the chair to retain the patient in position while affording substantial freedom of movement by the patient.

4 Claims, 4 Drawing Figures

Fig. 3.
Fig. 4.
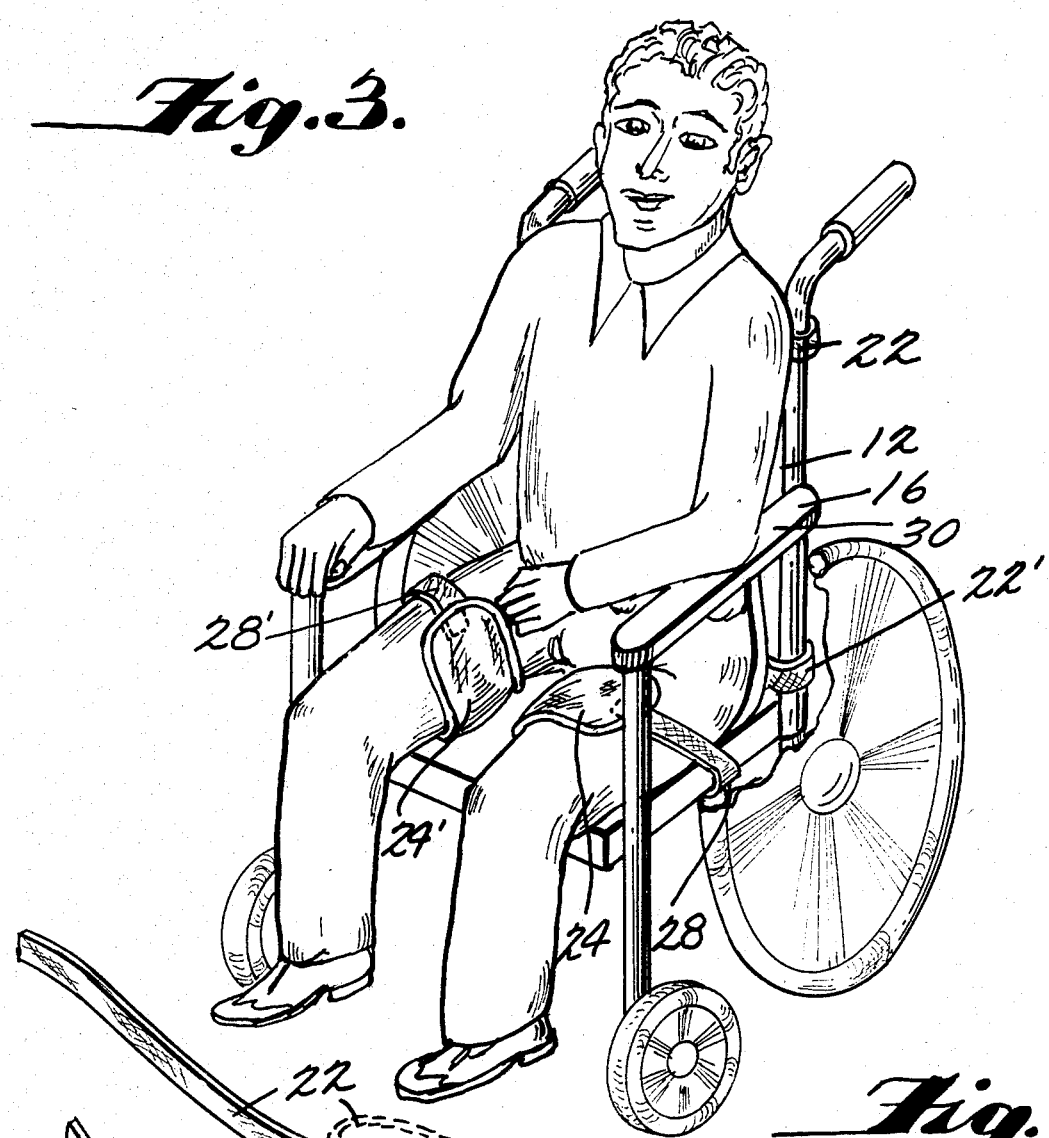
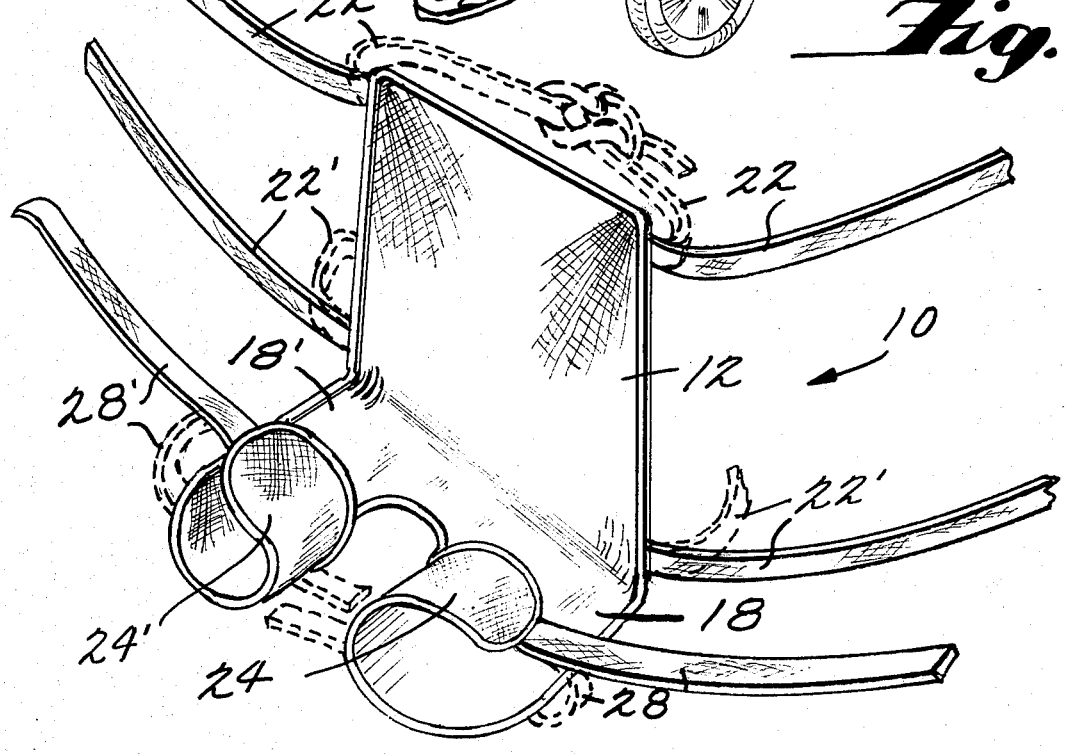

WHEEL CHAIR RESTRAINT

This invention relates to a restraining aid and more particularly to a restraint for use with wheel chairs and other chairs having seats and backs wherein the patient is prevented from sliding forward in the chair.

Many types of chair restraining devices have been developed in the past, but many of these devices unnecessarily restrict the movement of the patient. Other devices restrain the patient in uncomfortable ways, and still other known restraints are comprised of multiple pieces which are sewn or otherwise connected together in a way that can result in tearing or separation of the various parts of the restraint.

It is, therefore, an object of the present invention to provide a restraint for use with wheel chairs and other chairs having seats and backs.

Another object is to provide such a restraint which is preferably formed from a single, integral piece of wear-resistant cloth or fabric material which can be easily cleaned.

A further object of the invention is the provision of such a restraint which wraps only about the thighs of a patient.

Still another object is to provide such a restraint which provides for maximum freedom of movement of the patient while the patient is prevented from sliding forward in the chair.

Yet another object of the present invention is the provision of such a restraint which is easy to use and inexpensive to manufacture.

Additional objects and advantages of the invention will be set forth in part in the description which follows, and in part will be obvious from the description, or may be learned by practice of the invention. The objects and the advantages are realized and attained by means of the instrumentalities and combinations particularly pointed out in the appended claims.

To achieve these and other objects the present invention provides a restraint comprising a flexible first portion for placement against the back of a chair and against which a patient's back may rest; first and second flexible and distinct extension portions integral with and projecting forwardly from the first portion for placement onto the seat of the chair and upon which the thighs of the patient may rest; means in operative relationship with the first portion for removably securing the first portion to the chair; a first flexible restraining strap portion integral with the first extension portion and positioned to be selectively wrapped upwardly about an inner portion of a first thigh of the patient and over the thigh; means in operative relationship with the first strap portion for removably securing the first strap portion to the chair; a second flexible restraining strap portion integral with the second extension portion and positioned to be selectively wrapped upwardly about an inner portion of a second thigh of the patient and over the thigh; and means in operative relationship with the second strap portion for removably securing the second strap portion to the chair.

In accordance with the invention, the means for securing the first portion to the chair comprises a first plurality of straps attached to the first portion and positioned to enable the straps to be fastened together about the chair back.

Preferably, the means in operative relationship with the second strap portions for securing the first and second strap portions to the chair include first and second fastening straps secured to and extending from the first and second strap portions, respectively.

It is to be understood that both the foregoing general description and the following detailed description are exemplary and explanatory but are not restrictive of the invention.

The accompanying drawings, which are incorporated in and constitute a part of this specification, illustrate an example of a preferred embodiment of the invention, and together with the description, serve to explain the principles of the invention.

FIG. 3 is a perspective view showing a patient seated and restrained in a wheel chair by the restraint; and FIG. 4 is a perspective view of the restraint and showing its position when attached to a wheel chair and when restraining a patient in the wheel chair.

Figure 1:
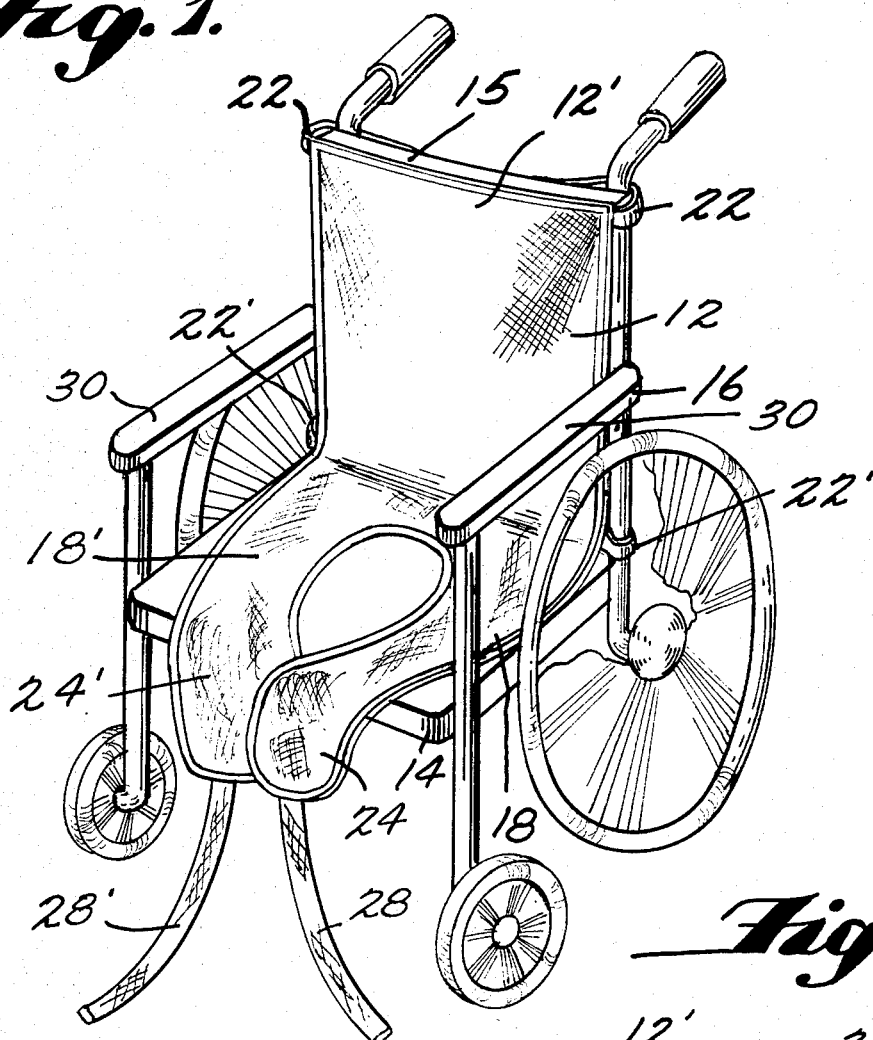
FIG. 1 is a perspective view of a wheel chair with the restraint attached to the chair.
Figure 2:
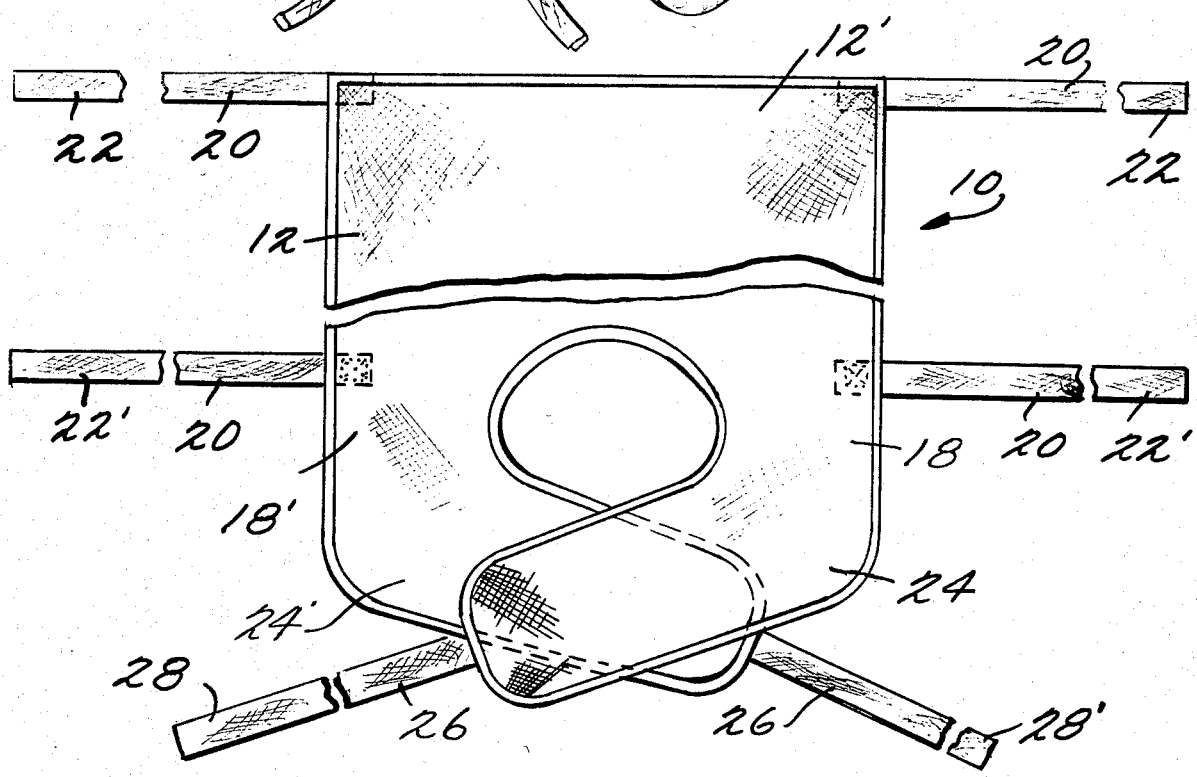
FIG. 2 is a top plan view of the wheel chair restraint as it appears when placed onto a flat surface.

With reference now to the drawings, wherein like reference characters designate like or corresponding parts throughout the several views, there is shown a restraint 10 for use with wheel chairs and other chairs having seats and backs. Restraint 10 includes a flexible first portion 12 for placement against the back 15 of chair 16 and against which the patient's back rests.

First and second flexible and distinct extension portions 18, 18' are integral with and project forwardly from first portion 12 for placement onto chair seat 14 and upon which the thighs of the patient may rest. Means 20 are provided in operative relationship with first portion 12 for removably securing first portion 12 to chair 16. Securing means 20 preferably include a first plurality of straps 22, 22' attached to first portion 12 and positioned to enable straps 22, 22' to be fastened together behind chair back 15. Various types of conventional fastening elements (not shown) may be used with straps 22, 22' to facilitate fastening the straps together. For example, straps 22, 22' may include buckles or Velcro whereby the straps can be easily and quickly fastened together and unfastened. Or, the straps can merely be tied together without the use of buckles, Velcro or any other fastening elements.

A first flexible restraining strap portion 24 is provided which is integral with first extension portion 18 and is positioned to be selectively wrapped upwardly about an inner portion of a first thigh of a patient and at least partially over the thigh. A second restraining strap portion 24' is similarly provided which is integral with second extension portion 18' and is positioned to be selectively wrapped upwardly about an inner portion of a second thigh of the patient and at least partially over the second thigh. Means 26 are provided in operative relationship with first and second strap portions 24, 24' for removably securing strap portions 24, 24' to chair 16. Securing means 26 preferably include first and second fastening straps 28, 28' which are secured to and extend from strap portions 24, 24', respectively.

Restraint 10 is preferably comprised of a cloth or fabric material which is easily washable and which is wear-resistant. For example, the fabric is preferably a bottom weight fabric of linen, chino or duck which is edged by double fold bias tape. Straps 22, 22', 28 and 28' are preferably nylon belting which is one inch wide.

When using restraint 10, the restraint is placed into chair 16 with first portion 12 resting against back 15 of the chair. Straps 22 are looped behind chair back 15 above the arms of the chair and are fastened together in a conventional manner. Straps 22' are looped behind chair back 15 at the base of the chair back and are fastened together in a conventional manner. In this way, the restraint is firmly attached to chair 16.

The patient is then seated in the chair, as shown in FIG. 3, and the patient's thighs are naturally positioned to rest upon extension portions 18, 18'. Restraining strap portions 24, 24' are wrapped upwardly about inner portions of the thighs of the patient and at least partially over the patient's thighs. Restraining straps 24, 24' are secured in position by means of fastening straps 28, 28', which are attached to legs, a cross bar or other portions of chair 16.

A patient is held in position in the chair in a manner which is also comfortable for the patient. The patient retains normal freedom of movement of the trunk and abdominal portions of his body, and restraint 10 comfortably and safely retains the patient in position in the chair.

The invention in its broader aspects is not limited to the specific details shown and described and departures may be made from such details without departing from the principles of the invention and without sacrificing its chief advantages.

What is claimed is:

1. A restraint for use with wheel chairs and other chairs having seats and backs, said restraint comprising:

a flexible first portion for placement against the back of said chair and against which a patient's back may rest;

first and second flexible and distinct extension portions integral with and projecting forwardly from said first portion for placement onto the seat of said chair and upon which the thighs of said patient may rest;

means in operative relationship with said first portion for removably securing said first portion to said chair;

a first flexible restraining strap portion integral with said first extension portion and positioned to be selectively wrapped upwardly about an inner portion of a first thigh of the patient;

means in operative relationship with said first strap portion for removably securing said first strap portion to said chair;

a second flexible restraining strap portion integral with said second extension portion and positioned to be selectively wrapped upwardly about an inner portion of a second thigh of the patient; and means in operative relationship with said second strap portion for removably securing said second strap portion to said chair.

2. A restraint as in claim 1 wherein said means for securing said first portion to said chair comprises a first plurality of straps attached to said first portion and positioned on said first portion to enable said straps to be fastened together about said chair back.

3. A restraint as in claim 2 wherein said means in operative relationship with said first and second strap portions for securing said first and second strap portions to said chair include first and second fastening straps secured to and extending from said first and second strap portions, respectively.

4. A restraint as in claim 3 wherein said restraint is comprised of a cloth or fabric material.

* * * * *